United States Patent
Miltenyi et al.

(12) 
(10) Patent No.: US 6,468,432 B1
(45) Date of Patent: Oct. 22, 2002

(54) METHODS OF MODIFICATION OF SELECTED CELLS IN A MAGNETIC CELL SEPARATION COLUMN

(75) Inventors: Stefan Miltenyi, Bergisch Gladbach (DE); Mario Assenmacher, Bergisch Gladbach (DE); Jürgen Schmitz, Bergheim (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

(21) Appl. No.: 09/654,186

(22) Filed: Sep. 1, 2000

Related U.S. Application Data

(60) Provisional application No. 60/152,408, filed on Sep. 3, 1999.

(51) Int. Cl.$^7$ .............................. C02F 1/48; C02F 1/00; B01D 27/02; G01N 33/53; G01N 33/553
(52) U.S. Cl. ..................... 210/695; 210/806; 210/222; 210/496; 435/7.1; 435/6; 435/30; 435/455; 436/526; 436/806
(58) Field of Search ............................ 435/4, 7.1, 7.2, 435/7.21, 30, 29, 325; 436/526, 63, 806, 496; 210/222, 223, 695

(56) References Cited

U.S. PATENT DOCUMENTS

| | | |
|---|---|---|
| 5,411,863 A | 5/1995 | Miltenyi |
| 5,622,831 A | 4/1997 | Liberti et al. |
| 5,691,208 A | 11/1997 | Miltenyi et al. |
| 5,705,059 A | 1/1998 | Miltenyi |
| 5,876,593 A | 3/1999 | Liberti et al. |
| 5,912,177 A | 6/1999 | Turner et al. |

FOREIGN PATENT DOCUMENTS

| | | |
|---|---|---|
| EP | 0 670 185 | 9/1995 |
| WO | WO 94/11078 | 5/1994 |
| WO | WO-9708557 | * 3/1997 |
| WO | WO 97/17611 | 5/1997 |
| WO | WO-9805791 | * 2/1998 |

OTHER PUBLICATIONS

Miltenyi et al. High Gradient Magnetic Cell Separation with MACS. Cytometry vol. 11. 1990 pp. 231–238.*

Anonymous (1997). "Separation Columns for MiniMACS, MidiMACS, VarioMACS, and SuperMACS," *Miltenyi Biotec GmbH catalogue*, Miltenyi Biotec GmbH, p. 8.1.

Gee, Adrian P. (1998). "Immunomagnetic Cell Separation Using Antibodies and Superparamagnetic Microspheres," Part IV, Chapter 9 in *Cell Separation Methods & Applications*, Recktenwald et al., eds., Marcel Dekker, Inc., New York, pp. 175–208.

Kantor, Aaron B. et al. (1998). "Magnetic Cell Sorting with Colloidal Superparamagnetic Particles," Part IV, Chapter 8 in *Cell Separation Methods & Applications*, Recktenwald et al., eds., Marcel Dekker, Inc., New York, pp. 153–173.

Lebkowski, Jane S. et al. (1998). "Isolation, Activation, Expansion and Gene Transduction of Cell Based Therapeutics Using Polysterene Immunoaffinity Devices," Part III, Chapter 4 in *Cell Separation Methods and Applications*, Recktenwald et al., eds., Marcel Dekker, Inc., New York, pp. 61–85.

\* cited by examiner

*Primary Examiner*—Remy Yucel
*Assistant Examiner*—Konstantina Katcheves
(74) *Attorney, Agent, or Firm*—Morrison & Foerster LLP

(57) ABSTRACT

A method is provided for modifying cells retained in a high gradient magnetic cell separation column (HGMS). Selected cells within a heterogeneous mixture are labeled with a label comprising a magnetic particle and specific for the selected cells. The labeled, selected cells are applied to the magnetic cell separation column, which retains the selected cells. The selected cells are then modified while retained in the column and then removed to the original suspension or to a purified, homogenous suspension.

20 Claims, 16 Drawing Sheets

METHODS OF MODIFICATION OF SELECTED CELLS IN A MAGNETIC CELL SEPARATION COLUMN

CROSS-REFERENCE TO RELATED APPLICATIONS

This application claims priority to U.S. Provisional Patent Application Ser. No. 60/152,408 filed Sep. 3, 1999, the full disclosure of which is incorporated herein by reference.

TECHNICAL FIELD

The present invention relates to the use of high-gradient magnetic cell separation (HGMS) techniques in the process of modifying selected cells.

BACKGROUND ART

The prior art addresses various methods and techniques to modify cells outside the body. Surface staining of cells by the attachment of antibodies bound to fluorescent moieties is one frequent modification. Intracellular staining after fixation is also common. Kappa and lambda light chains can be targeted by such stains and used to assay for monoclonal tumor cell populations. While stains of this sort are frequently specific, cells can be modified in myriad non-specific ways, such as by exposure to a pharmacological or chemical agent, treatment with a hormone or other compound known to mediate cellular activity, or transfection with genes to bring about a recombinant product. Cell modification techniques thus have both research-oriented and treatment-oriented potential.

In the prior art, modifications like staining are performed either with cells in suspension or with monolayers of cells immobilized on different surfaces (such as a microscope slide), to allow the modifying agent to access all the cells equally. Staining or otherwise modifying cells in these fashions are known in the art. Recent advancements in monolayer modification are exemplified by Lebkowski, et al., *Isolation, Activation, Expansion and Gene Transduction of Cell Based Theraputics Using Polysterene Immunoaffinity Devices*, in Cell Separation Methods and Applications, Recktenwald, et al., eds. (1998) and in U.S. Pat. No. 5,912,177. However, these methods can be time-consuming and often involve multiple washing steps, creating a potential risk of cell loss. These methods are especially problematic where small numbers of cells are involved.

In the prior art, it is not recommended to modify cells in aggregate forms (such as the pellet formed after centrifugation). Crosslinking agents such as formaldehyde pose similar problems, as cells need to be separated from each other to prevent irreversible aggregation.

Very frequently, the practitioner will wish to modify one cell type within a heterogeneous mixture or suspension, such as lymph or blood, because subsequent to modification that specific cell type is to be studied or returned to the patient as part of a treatment or test regiment. In such circumstances, modification of cells other than the targeted class can have adverse effects. Various methods of cell separation have evolved to meet these needs.

An overview of cell separation techniques current in the art is provided by Cell Separation Methods and Applications, Recktenwald, et al., eds. (1998). One cell separation technique used involves magnetic cell separation, whereby target cells may be labeled with a magnetic marker and then selectively retained in a chamber or column exposed to a magnetic field. Kantor, et al. (1998, *Magnetic Cell Sorting with Colloidal Superparamagnetic Particles,* in Cell Separation Methods & Applications); Gee (1998, *Immunomagnetic Cell Separation Using Antibodies and Superparamagnetic Microspheres* in Cell Separation Methods & Applications); and Miltenyi, S., U.S. Pat. No. 5,411,863, disclose magnetic cell separation techniques. For high gradient magnetic separation, typically a heterogeneous suspension, containing selected cells bound to magnetic markers, is passed through a column, allowing the selected cells to adhere magnetically to the column or to a paramagnetic matrix within the column. The remainder of the suspension is eluted, leaving the selected, magnetized cells bound to the column. When the magnetic field is removed, the selected cells can be eluted.

Non-magnetic cell separation processes may be used to facilitate cell modification. These methods include immunoaffinity cell separation techniques, which are often less preferable than magnetic cell separation methods, because the former often result in increased cell loss as well as increased reagent use and salt concentration, which may require dialysis of the eluate. Lebkowski, et al. (1998, *Isolation, Activation, Expansion, and Gene Transduction of Cell-Based Therapeutics Using Polystyrene Immunoaffinity Devices,* in Cell Separation Methods and Applications) disclose a method whereby selected classes of peripheral blood mononuclear cells (PBMC) can be positively selected by immunoaffinity processes, in which the selected cells are immobilized by monoclonal antibodies or lectins covalently bound to polystyrene structures and then cultured, activated, or genetically modified while immobilized. A similar method for modifying stem cells is disclosed in U.S. Pat. No. 5,912,177. A central disadvantage of these methods, however, is that they bind the selected cells to a flat or otherwise two-dimensional surface, requiring a substantial surface area in relation to the number of cells to be selected. The cells must form a monolayer, as illustrated in FIG. 1. Furthermore, antibodies used for selection are affixed to the device itself and such techniques require a specific device or structure for each desired target. Moreover, releasing and resuspending selected cells from those structures can be a time consuming process.

Magnetic cell separation techniques have been used to immobilize cells as described in U.S. Pat. No. 5,622,831 and U.S. Pat. No. 5,876,593. U.S. Pat. No. 5,622,831, requires a complicated switching mechanism to release and resuspend immobilized cells and U.S. Pat. No. 5,876,593 does not employ a column, but instead requires immobilizing the cells as a substantially one-dimensional monolayer.

It would be advantageous to modify selected cells in a HGMS column, which would convey the additional advantages of the magnetic system over the immunoaffinity system, such as simple resuspension of immobilized cells, increased cell concentration, decreased reagent use, and greater effective concentration of modifying reagents.

DISCLOSURE OF THE INVENTION

The present invention provides methods for modifying selected cells comprising modifying magnetically labeled selected cells retained on a high gradient magnetic separation (HGMS) column thereby producing modified, selected cells. The present invention also provides methods for modifying selected cells comprising the steps of applying a population of cells to a HGMS column wherein said population of cells comprises magnetically labeled selected cells and wherein said magnetically labeled selected cells are retained by said column; and modifying said selected cells retained by said column thereby producing modified, selected cells. In other aspects, the methods further comprise removing the modified, selected cells from the column. In a further aspect, the invention comprises the additional steps of applying the removed, selected cells to a second high gradient magnetic cell separation column such that the selected cells are retained by said second column; and modifying the selected cells retained by said second column.

In other embodiments, the high gradient magnetic cell separation column contains a high volume of a matrix relative to the total volume of the column. In additional embodiments, the matrix is more than 50% of the total volume of the column and in yet further embodiments, more than 60% of the total volume of the column. In yet additional embodiments, the matrix comprises ferromagnetic spheres. In other embodiments, the removing is by removing said magnetic field.

In some embodiments, the modifying comprises intracellular staining of the selected cells; permeabilizing the selected cells; labeling the magnetically labeled selected cells with a second label; binding a biologically reactive compound to the selected cells; transfecting the selected cells with an expression vector comprising a gene of interest; applying an enzyme to the selected cells; applying a pharmacological agent to the selected cells; applying a biological or chemical agent to the selected cells; or applying multiple modifying agents. In some embodiments, the biologically reactive compound includes antibodies, ligands, proteins, peptides, nucleic acids, polynucleotides, oligonucleotides, lectins, lipids or enzymes.

BRIEF DESCRIPTION OF THE DRAWINGS

FIG. 4A shows CD138.PE versus PI staining of PMBC spiked with U266 myeloma cells before separation on a MACS® high gradient magnetic cell separation; FIG. 4B shows CD138.PE staining versus FL3 (the FL3 channel of the flow cytometer collects fluorescent light at equal to or greater than 650 nm) of fixed positive cell fraction after second separation on a MACS® high gradient magnetic cell separation with gating on CD138 positive cells; and 4C shows intracellular staining of human immunoglobulin lambda light chain versus CD138.PE staining on gated cells.

FIG. 5A shows CD138.PE staining of live leukocytes before separation on MACS® high gradient magnetic cell separation versus FL1-H (the FL1-H channel of the flow cytometer collects fluorescent light between 525–545 nm); FIG. 5B shows CD138.PE staining of live leukocytes after separation on MACS® high gradient magnetic cell separation versus FL1-H; FIG. 5C shows Forward Scatter (FSC) versus Sideward Scatter (SSC) signals of leukocytes before separation; and FIG. 5D shows FSC/SSC signals of positive cell fraction.

FIGS. 6A and 6B show CD138.PE staining versus FL3 autofluorescence of positive fraction of fixed cells after second separation on MACS® high gradient magnetic cell separation with gating (according to R1) on CD138 positive cells; FIG. 6C shows intracellular staining of human immunoglobulin lambda light chain versus CD138.PE staining on gated cells; and FIG. 6D shows intracellular staining of human immunoglobulin kappa light chain versus CD138.PE staining on gated cells.

FIG. 7A shows goat anti-human lambda.FITC staining of cells stained on a MACS® high gradient magnetic cell separation column; and FIG. 7B shows goat anti-human lambda.FITC staining of cells stained outside of a MACS® high gradient magnetic cell separation column.

FIG. 8A shows staining of CD19.Cy5™ versus CD138.PE before MACS® high gradient magnetic cell separation; FIG. 8B shows staining of CD19.Cy5? versus CD138.PE of positive cell fraction after MACS® high gradient magnetic cell separation; FIG. 8C shows surface IgA.FITC staining versus CD138.PE of positive cell fraction gated on CD138 positive cells; FIG. 8D shows surface IgM. FITC staining versus CD138.PE of positive cell fraction gated on CD138 positive cells; and FIG. 8E shows surface IgG.FITC staining versus CD138.PE of positive cell fraction gated on CD138 positive cells.

FIG. 9A shows FSC/SSC signals of positive cell fraction with gating on lymphocytes; FIG. 9B shows staining of CD19.PE versus LDS of positive cell fraction with LDS gate on nucleated cells; and FIG. 9C shows staining of CD4.FITC versus CD19.PE of positive cells gated by R1 and R2.

BEST MODE FOR CARRYING OUT THE INVENTION

Figure 1:
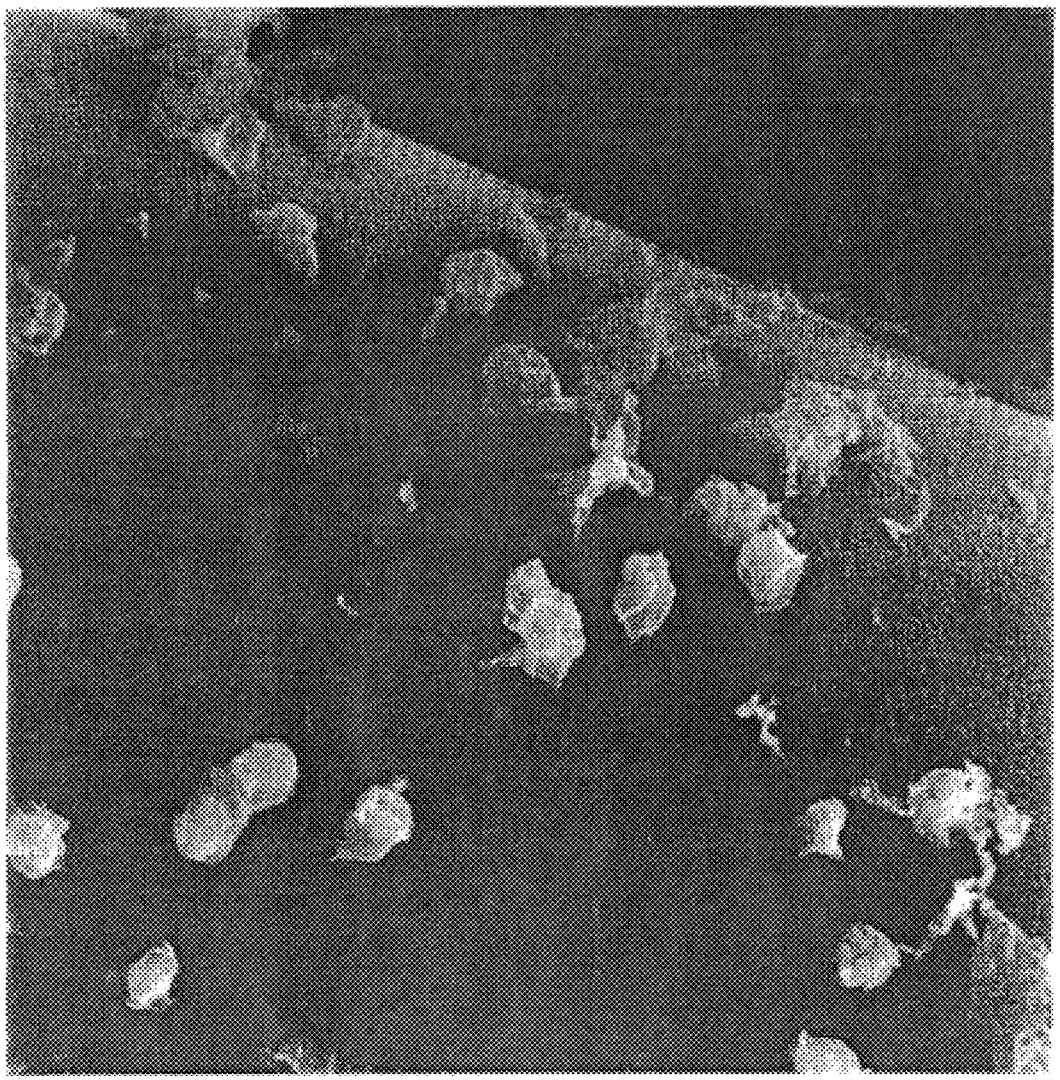
FIG. 1 shows cells immobilized under the prior art teachings of Lebkowski, et al.

The present invention provides a process for modifying selected cells by modifying selected cells retained in a high gradient magnetic cell separation (HGMS) column. The present invention is concerned with positive selection, that is, the modification of a specific cell population that has been subject to direct selection. By performing the methods on a population of cells, such as whole blood, that comprise the selected cells, the selected cell population can be enriched. The present invention substantially reduces the number of steps necessary as compared to the prior art, in which enrichment and modification processes are undertaken separately.

The invention employs a HGMS column device or methodology that is intended to permit specificity for selected cells or labeled selected cells. One particular advantage of the invention is the increased cell concentration that can be used with the HGMS system and the reduction in the number of steps in the method. For example, in some aspects of the invention, a sample, such as whole blood, is obtained directly from an organism, cells are selected, such as by magnetic labeling in whole blood, the whole blood is applied to an HGMS, the selected cells retained on the column are modified, and the modified, selected cells are eluted and proceed to analysis without an intervening centrifugation step, thereby providing an opportunity for automation and decreasing the potential for cell loss.

Another advantage of the invention is the opportunity to control temperature during the process. The HGMS can proceed in an incubator or refrigerator and/or with the use of buffers at the desired temperature. The use of an HGMS matrix comprising a heat-conducting matrix, including for example, steel balls, steel wool or other spheres, provides the opportunity for controlling temperature during the process.

Another advantage of the invention is that cells can be rapidly moved from phase to phase on the HGMS column, that is, from mobile phase to immobile phase or immobile phase to mobile phase, by switching the magnetic field on and off or by changing the magnetic field. In a preferred embodiment, the magnetic field can be adjusted by moving the column relative to the magnet or alternatively, by modifying an electromagnet.

Definitions

As used herein, "selected cells" are those cells the practitioner desires to modify. Typically, the cells will bear some characteristic that differentiates them from other cells in a heterogeneous suspension, and that will enable them to be labeled and separated. According to the invention, the selected cells are retained on an HGMS column, modified while retained on the column, then eluted. "Retention" of selected cells ensures that the selected cells remain in the column while unwanted cells are removed. Typically, the retention of the selected cells is by immobilization.

As used herein, "immobilizing" selected cells in a magnetic cell separation column refers to the retention of the cells in the column in a substantially fixed position. "Removing" selected cells from a magnetic cell separation column involves eluting the selected cells subsequent to retention or immobilization. In situations where a high purity of selected cells is desired, the selected cells may be removed and resuspended in a suitable buffer. Alternatively, selected cells may be removed and returned to the original suspension after modification of the selected cells in the column as described herein.

As used herein, "labeling" is the process of affixing a marker to cells, allowing, sometimes after further processing, those cells to be separated from a heterogeneous suspension and/or detected, analyzed or counted. Labels can be specifically targeted to selected cells, but need not be. Such markers or labels include, but are not limited to, colored, radioactive, fluorescent, or magnetic molecules or particles conjugated to antibodies or other biological molecules or particles known to bind to cells or cellular components. Antibodies are often used as label components because of their ability to target specific cell types. Other biologically reactive label components that can serve as alternatives to antibodies include, but are not limited to, genetic probes, proteins, peptides, amino acids, sugars, polynucleotides, enzymes, coenzymes, cofactors, antibiotics, steroids, hormones or vitamins.

As used herein, "magnetically labeling" a cell means to affix a magnetic label to a cell, such labeling being accomplished by affixing a particle or molecule with magnetic properties to said cell. In one embodiment, the magnetic label comprises an antibody conjugated to a magnetic particle. Magnetic labels comprising an antibody conjugated to a magnetic particle are commercially available from Miltenyi Biotec GmbH (Friedrich Ebert Str. 68, D-51429 Bergisch Gladbach, Germany). Such a label can optionally include a fluorescent or radioactive particle or component as well.

As used herein, a "magnetic cell separation column" is a high gradient magnetic separation (HGMS) column. HGMS columns are described, for example, in Miltenyi, S., U.S. Pat. No. 5,411,863, entitled Methods and Materials for Improved High Gradient Magnetic Separation of Biological Materials and are commercially available from Miltenyi Biotec GmbH (Friedrich Ebert Str. 68, D-51429 Bergisch Gladbach, Germany).

Figure 3A:
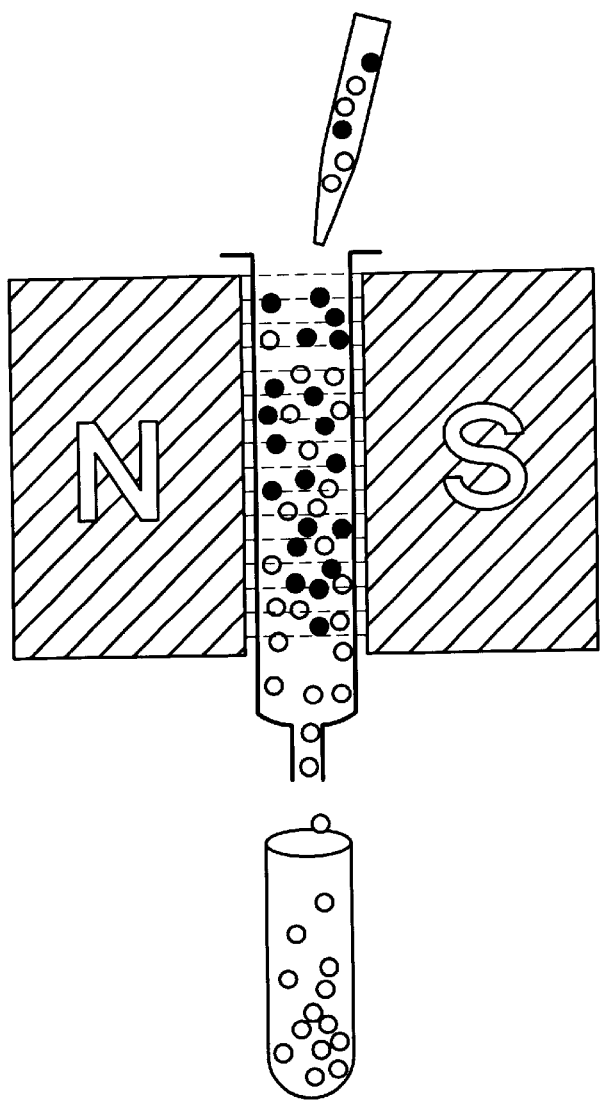
FIGS. 3A–3B are a series of representational drawings. 3A depicts a mixture of labeled and unlabeled cells applied to a magnetic cell separation column means (depicting north and south magnetic fields) permitting elution of unlabeled cells and retention of labeled cells in the column. 3B depicts removal of the magnetic field and elution of labeled cells into a separate suspension.
Figure 3B:
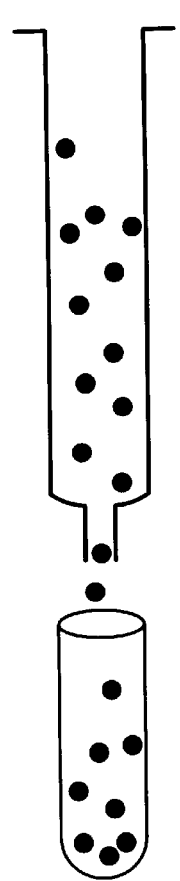

As used herein, "high gradient magnetic cell separation" is a procedure for selectively retaining magnetic materials in a chamber or column disposed in a magnetic field, which can also be applied to non-magnetic targets selectively labeled with magnetic particles. In the presence of a magnetic gradient supplied across the chamber, the magnetically labeled target is retained in the chamber. If the chamber contains a matrix, the magnetically labeled target becomes associated with the matrix. Materials which do not have magnetic labels pass through the chamber. The retained materials can then be eluted (removed) by changing the strength of, or by eliminating, the magnetic field. For magnetically labeled targets, release is also possible by other means, such as with magnetic beads further comprising an enzymatic cleavage site, wherein enzymatic cleavage (either inside or outside the column) releases the magnetic targets. Alternatively, retained materials can be released by, for example, a change of pH, or change in ionic strength. The process of retention and release of selected cells is illustrated in FIGS. 3A–3B. The magnetic field can be supplied either by a permanent magnet or by an electromagnet. The selectivity for a desired target material is supplied by the specific binding partner conjugated to the magnetic particle. The chamber across which the magnetic field is applied is often provided with a matrix of a material of suitable magnetic susceptibility to induce a high magnetic field gradient locally in the chamber in volumes close to the surface of the matrix. This permits the retention of fairly weakly magnetized particles. See Miltenyi, S., U.S. Pat. No. 5,411,863.

Preferably, the magnetic cell separation column will employ a column containing a high volume of matrix. Matrix is supplied to provide a strong local magnetic field gradient, and is frequently a ferromagnetic material such as a polymer coated steel wool. Preferably, a closely packed matrix of ferromagnetic spheres coated with a biocompatible polymer is employed. See Kantor, et. al, *Magnetic Cell Sorting with Colloidal Superparamagnetic Particles* in Cell Separation Methods and Applications (1998). Matrix volume is preferably more than 50% of the total column volume and preferably more than 60% of the total column volume. Commercially available MS+ or VS+ columns (Miltenyi Biotec GmbH, Friedrich Ebert Str. 68, D-51429 Bergisch Gladbach, Germany), containing iron-sphere matrices, provide high capacity of bound cells with low free column volume, as detailed in Table 1.

TABLE 1

| Column | Bound Cells | Total Vol. | Free Column Vol. |
|---|---|---|---|
| MS+ | up to $10^7$ | about 150 µl | 70 µl |
| VS+ | up to $10^8$ | about 1.2 ml | 500 µl |

Having been immobilized within the column, the selected cells can be modified by the practitioner while they are retained.

As used herein, "modifying" cells refers to any process of physically, biologically or chemically altering selected cells from their previous state. Examples of modifications within the scope of the invention include, but are not limited to, labeling cells (with such labels as antibodies or fluorescent or radioactive markers or biological ligands and substrates), intracellular staining, surface staining, fixation, permeablization, genetic recombination, activation, transfection, infection, and other cellular changes caused by applying enzymes, biological modifiers, or pharmacological or chemical agents.

As used herein, a "modifying agent" broadly refers to any agent capable of bringing about a modification. Such modifying agents can include, but are not limited to, antibodies, ligands, proteins, peptides, nucleic acids, oligonucleotides, polynucleotides, lectins, lipids, biological modifiers, fixation agents, pharmacological agents, chemical agents, permeabilization agents, intracellular stains, surface stains, expression vectors, and enzymes.

As used herein, "fixation" or "fixing" refers to any process that serves to preserve a cell in a certain state, preferably resulting in maintaining an accurate representation of the structure of the cell in vivo, such as by maintaining its original size, suffering minimal loss of cellular materials, or retaining the reactivity of its intracellular constituents. Preferred fixing agents include formaldehyde solutions, formalin, glutaraldehyde and others. Formaldehyde fixation preferably includes an incubation step, where the formaldehyde solution is given time to penetrate the cells at an optimum temperature. Although formaldehyde fixation can be accomplished while cells are retained in a cell separation column, it is preferably accomplished with cells prior to application to the column. The fixation can be performed before or after magnetic labeling. After the fixation and incubation steps, the cells may be directly applied to the cell separation column for separation and for further modification on the column. This reduces formation of aggregates, which can occur when fixation is performed on cells immobilized in a column.

As used herein, "intracellular staining" refers to the process of binding a label to an intracellular molecule, component or structure, including but not limited to proteins, enzymes, nucleotides, chromosomes, immunoglobulins or immunoglobulin components, or membranes. Typically, cells are permeabilized prior to intracellular staining.

As used herein, "permeabilization" of a cell refers to any process which facilitates access to cellular cytoplasm or intracellular molecules, components or structures of a cell. Permeabilization can be by any method known in the art, including, but not limited to, exposure to formaldehyde, ethanol or detergents. Saponin in buffer has been used successfully in accordance with the invention.

As used herein, "transfection" is the genetic modification of cultured cells by the uptake of DNA, which is usually applied in the form of plasmids or other types of DNA vectors containing genes of interest. Transfection can be by any method known in the art, including but not limited to calcium phosphate- or DEA-dextran-mediated transfection, lipofection, or through the use of viral vectors, such as adenoviral or retroviral vectors.

A "vector" as used herein is a small carrier DNA molecule into which a DNA sequence can be inserted for introduction into a host cell where it will be replicated and/or expressed. Vectors can be derived from plasmids, bacteriophages, or plant or animal viruses.

As used herein, a "biological modifier" is any biological compound able to bring about a reaction or change in the activity a living cell. Such modifiers can accelerate or decelerate cellular activity, stimulate or retard mitosis, activate or deactivate certain genes, increase or reduce cell receptivity or permeability, or effect other change. Examples of biological modifiers include, but are not limited to, pharmacologic agents, cytokines, interleukins, hormones, growth factors, and other intercellular or intracellular signals.

As used herein, "pharmacological agents" are any of a number of substances available for the treatment of disease or dysfunction.

As used herein, "chemical agents" are any of a number of substances effecting a chemical reaction with a cell. Examples of chemical agents include, but are not limited to, acids, bases, stains, and solvents.

HGMS and Modification of Selected Cells

The invention herein is preferably accomplished by first labeling selected cells with a label comprising a magnetic particle, typically 20–100 nm in diameter. Such microbeads are commercially available as magnetic microbeads covalently conjugated to a variety of monoclonal antibodies (e.g., for example, MicroBeads from Miltenyi Biotec GmbH, Friedrich Ebert Str. 68, D-51429 Bergisch Gladbach, Germany) and the labeling is accomplished by means known in the art. Fluorescence labeling of selected cells can be performed at this stage as well. If possible, the cells are preferably washed at this stage and suspended in an appropriate buffer, such as PBS/BSA/EDTA.

Magnetically labeled selected cells are then applied to a high gradient magnetic cell separation (HGMS) column. HGMS columns are described in U.S. Pat. No. 5,411,863 and are commercially available as MACS® high gradient magnetic separation columns from Miltenyi Biotec GmbH (Friedrich Ebert Str. 68, D-51429 Bergisch Gladbach, Germany). However, any high gradient magnetic cell separation known in the art may be used in accordance with this invention.

The magnetic cell separation column retains the selected cells in the column, while allowing unlabeled cells (and other unwanted matter) to flow through. Typically, the column contains a ferromagnetic matrix and is placed in a strong external magnetic field, and the labeled, selected cells are magnetically immobilized on the matrix in the column. Preferably, the column is washed while the cells are immobilized to increase the homogeneity of the retained cell population.

Figure 2:
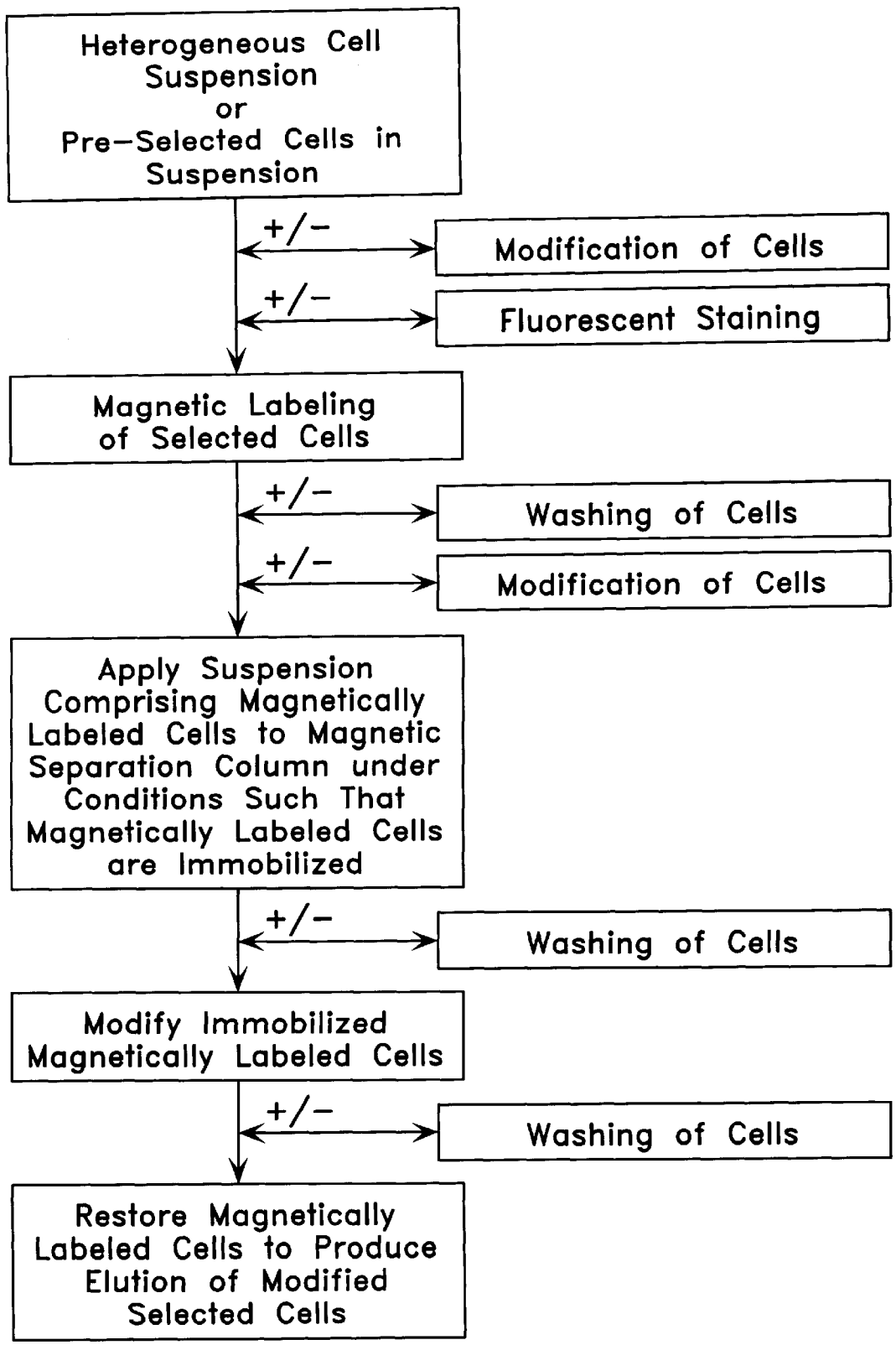
FIG. 2 is a flow chart of a typical modification process according to the present invention.

While selectively retained in the column, the selected cells are relatively homogenous. This provides an optimum setting for selective modification of these cells, since modifying agent concentration can be minimized while maximizing the efficiency of the modification. Moreover, successive or multiple modifications may be accomplished according to the invention. For example, the immobilized cells may be modified, rinsed, and then stained before being eluted from the column. Alternatively, immobilized cells may be modified, rinsed and removed, manipulated outside the column, then reapplied to a column, immobilized and stained, then removed once more. The modification can comprise fixation and/or permeabilization, subsequent to which additional modification such as intracellular staining can be performed. Other modifications include surface staining as described above and in the following examples. A flow chart describing this process is provided in FIG. 2.

The range of modifications is not limited to analytic or staining protocols; rather, any cellular modification known in the art can be adapted in accordance with this invention. Thus, for example, modification by the application of any modifying agent, biological modifier, pharmacological agent, chemical agent, or enzyme to the cells retained in the column, is within the scope of the invention. The following examples are provided to illustrate, but not limit, the scope of the invention.

EXAMPLES

Example 1

Fixation and Combined Intracellular and Surface Staining of CD-138 Positive Peripheral Blood Mononuclear Cells Peripheral blood mononuclear cells (PBMC) were mixed with cells of the CD138 expressing U266 myeloma cell line at a 200:1 ratio, i.e., resulting in 0.5% U266 cells among PBMCs. $5 \times 10^7$ Cells were labeled with mouse anti-CD138 mAb B-B4 conjugated MicroBeads (Miltenyi Biotec GmbH, Friedrich Ebert Str. 68, D-51429 Bergisch Gladbach, Germany) in 1000 µl PBS/BSA/EDTA (buffer) for 15 minutes at 8° C. Phycoerythrin conjugated mouse anti-CD138 mAb B-B4 (CD138.PE) (Miltenyi Biotec GmbH (Friedrich Ebert Str. 68, D-51429 Bergisch Gladbach, Germany) was added for an additional 5 minutes at 8° C. The cells were washed and resuspended in 500 µl buffer.

CD138 positive cells were enriched with the MACS® magnetic cell separation system (Miltenyi Biotec GmbH, Friedrich Ebert Str. 68, D-51429 Bergisch Gladbach, Germany). The magnetically labeled cell suspension was pipetted on top of a separation column in a MiniMACS separation unit (Miltenyi Biotec GmbH, Friedrich Ebert Str. 68, D-51429 Bergisch Gladbach, Germany). The cell suspension was allowed to pass through and the column was washed with 3×500 µl buffer. The effluent was collected as a negative fraction. The column was removed from the separator, and was placed on a suitable tube. 0.5 ml PBS/EDTA containing 2% formaldehyde (Merck) was pipetted on top of column and magnetically labeled cells were flushed out using a plunger. Eluted cells were incubated for 20 minutes at room temperature (RT) and directly applied on top of a second separation column in a MiniMACS separation unit. Cell suspension was allowed to pass through and column was washed with 2×500 µl buffer containing 0.5% saponin (saponin-buffer from Serva, Carl-Benz-Str. 7, 69115 Heidelberg, Germany). Effluent was collected as a negative fraction. Then 100 µl saponin-buffer containing 10 µg/ml Goat anti-human lambda.FITC (Southern Biotechnology Associates (SBA) 160A Oxmoor Boulevard, Birmingham, Ala. 35209, USA) and 2 µg/ml Phycoerythrin conjugated mouse anti-CD138 mAb B-B2 (Miltenyi Biotec GmbH, Friedrich Ebert Str. 68, D-51429 Bergisch Gladbach, Germany) were applied to the column and incubated for 10 minutes at room temperature. The column was washed with 1×500 µl saponin-buffer. The column was removed from separator, and placed on a suitable container to receive eluate. 0.5 ml of buffer was pipetted on top of column, and magnetically labeled cells were flushed out using a plunger.

In parallel, CD138 positive cells were enriched by two rounds of MiniMACS separation to compare separation efficiencies.

Original cells (i.e. before MACS® high gradient magnetic cell separation), negative cell fractions (of first as well as second MACS® high gradient magnetic cell separation) and positive cell fractions of the MACS® high gradient magnetic cell separation were analyzed by flow cytometry. FACScan and CELLQuest research software (Becton Dickinson, Mountain View, Calif.) were used for flow cytometric analysis. Dead cells and cell debris were excluded according to their scatter properties and staining with propidium iodide (PI; 0.3 µg/ml) for live cells.

Figure 4A:
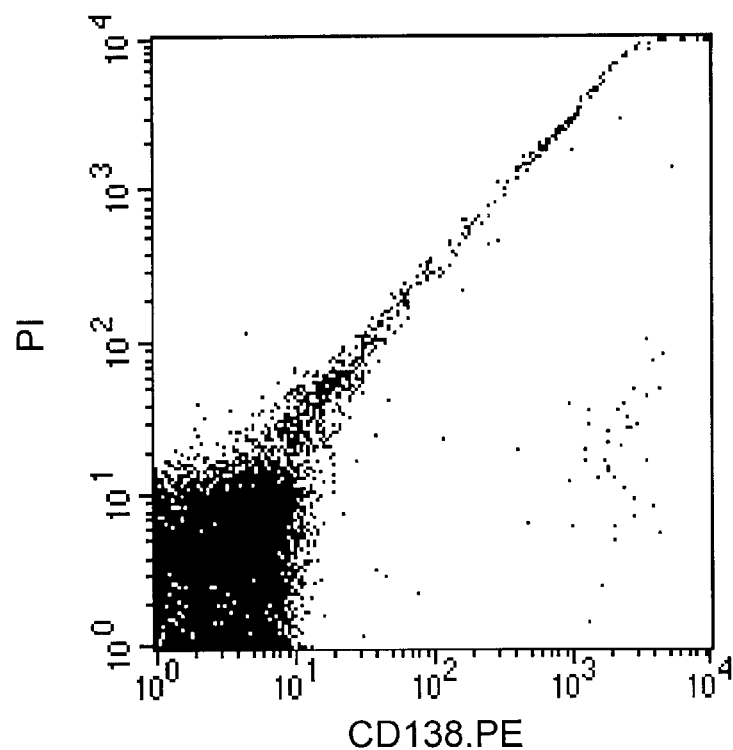
FIGS. 4A–4C are a series of FACS dot plots relating to the results of Example 1 showing intracellular staining of lambda light chain in isolated myeloma cells (U266) spiked into peripheral mononuclear blood cells.
Figure 4B:
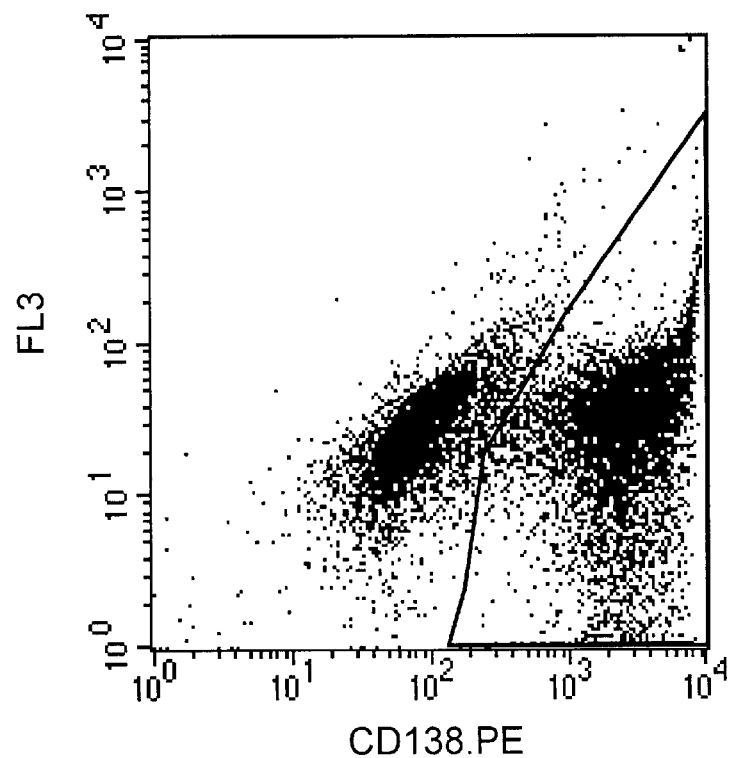
Figure 4C:
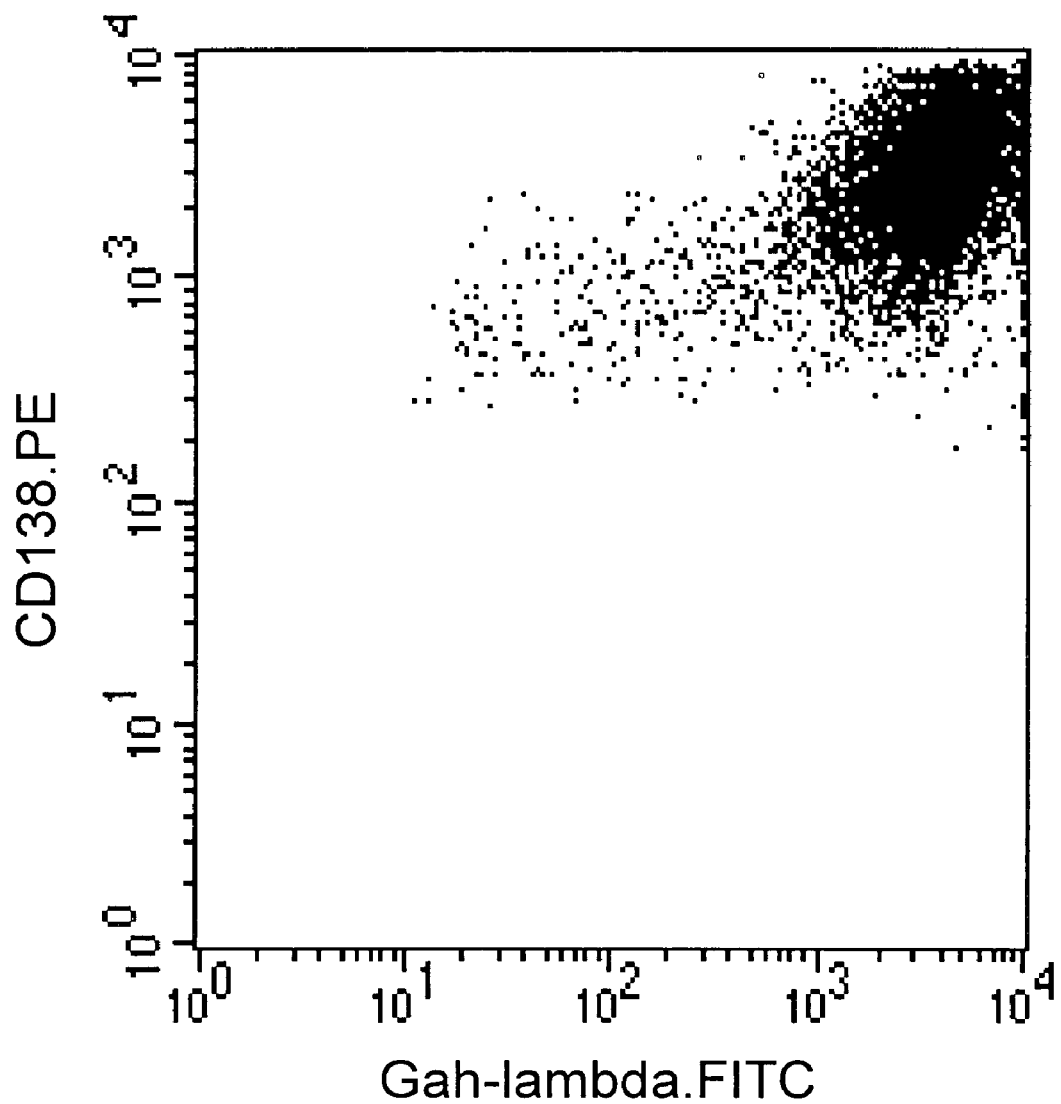

The results are shown in FIGS. 4A–4C. FIG. 4A shows CD138.PE versus PI staining of cells before MACS® high gradient magnetic cell separation. While in the control separation, CD138 positive cells were enriched up to 52% purity among all (ungated) cells (corresponding to 98% purity of live cells), CD138 positive cells were enriched to 64% purity among all (ungated) cells in the separation including fixation and intracellular staining. FIG. 4B shows CD138.PE staining versus FL3 autofluorescence of fixed positive cell fraction after second MACS® high gradient magnetic cell separation with gating on CD138 positive cells. The FL3 channel of the flow cytometer collects fluorescent light at equal to or greater than 650 nm. FIG. 4C shows intracellular staining of human immunoglobulin lambda light chain versus CD138.PE staining on gated cells. Nearly all CD138 positive cells express intracellular lambda light chain as reported for U266 cells. Also the recoveries of CD138+ cells in the positive fractions were very similar in both separations, with 81% and 91%, respectively. Thus the separation efficiencies were equivalent for both cases.

Example 2

Fraction and Intracellular Staining of Leukapheresis Sample

Leukapheresis sample of a multiple myeloma patient was labeled with mouse anti-CD138 mAb B-B4 conjugated MicroBeads (Miltenyi Biotec GmbH, Friedrich Ebert Str. 68, D-51429 Bergisch Gladbach, Germany) in PBS/BSA/EDTA (buffer) for 15 minutes at 8° C. Phycoerythrin conjugated mouse anti-CD138 mAb B-B4 (CD138.PE) (Miltenyi Biotec GmbH, Friedrich Ebert Str. 68, D-51429 Bergisch Gladbach, Germany) was added for an additional 5 minutes at 8° C. Cells were washed and resuspended in 2 ml buffer. CD138 is expressed on normal as well as malignant plasma cells.

CD138 positive cells were enriched with the MACS® high gradient magnetic cell separation. Magnetically labeled cell suspension was pipetted on top of a VS+ separation column in a MidiMACS separation unit (Miltenyi Biotec GmbH, Friedrich Ebert Str. 68, D-51429 Bergisch Gladbach, Germany), cell suspension was allowed to pass through and the column was washed with 3×3 ml buffer. Effluent was collected as a negative fraction. Column was removed from separator, and placed on a suitable tube. 5ml PBS/EDTA was pipetted on top of column and magnetically labeled cells were flushed out using a plunger. Part of the cells were directly applied to a second round of MiniMACS separation. To the other part of the cells ($5 \times 10^5$ cells in 1 ml) the same volume of buffer containing 4% formaldehyde (Merck) was added and incubated for 20 min at room temperature. Then the cells were split into two samples and applied directly on top of two separation columns in two MiniMACS separation units. The cell suspensions were allowed to pass through the columns and the columns were washed with 2×500 µl buffer containing 0.5% saponin (saponin-buffer, Serva, Carl-Benz-Str. 7, 69115 Heidelberg, Germany). The effluents were collected as negative fractions. Then 100 µl saponin-buffer containing 2 µg/ml CD138.PE and 10 µg/ml Goat anti human lambda.FITC (SBA, 160A Oxmoor Boulevard, Birmingham, Ala. 35209, USA) was applied to one column, and 100 µl saponin-buffer containing 2 µg/ml CD138.PE and 10 µg/ml Goat anti-human kappa.FITC (SBA, 160A Oxmoor Boulevard, Birmingham, Ala. 35209, USA) was applied to the other. Both columns incubated for 10 minutes at room temperature. The columns were washed with 1×500 µl saponin-buffer and 1×500 µl buffer. The columns were removed from separators, and placed on suitable tubes. 0.5 ml buffer was pipetted on top of each column and the magnetically labeled cells were flushed out using a plunger.

The original cells (i.e. before MACS® high gradient magnetic cell separation), the negative cell fractions (of the first as well as the second MACS® high gradient magnetic cell separation), and the positive cell fractions of the MACS® high gradient magnetic cell separation were analyzed by flow cytometry. FACScan and CELLQuest research software (Becton Dickinson, Mountain View, Calif.) were used for flow cytometric analysis. Dead cells and cell debris were excluded according to scatter properties and staining with propidium iodide (PI; 0.3 µg/ml) for live cells.

Figure 5A:
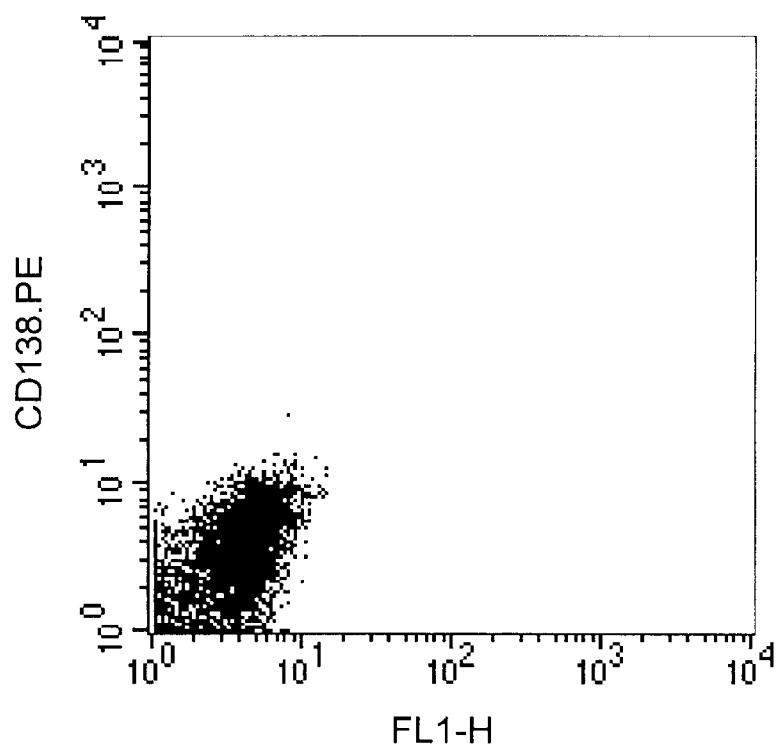
FIGS. 5A–5D are a series of FACS dot plots relating to the results of Example 2 showing isolation of CD138+ plasma cells from leukapheresis of a myeloma patient.
Figure 5B:
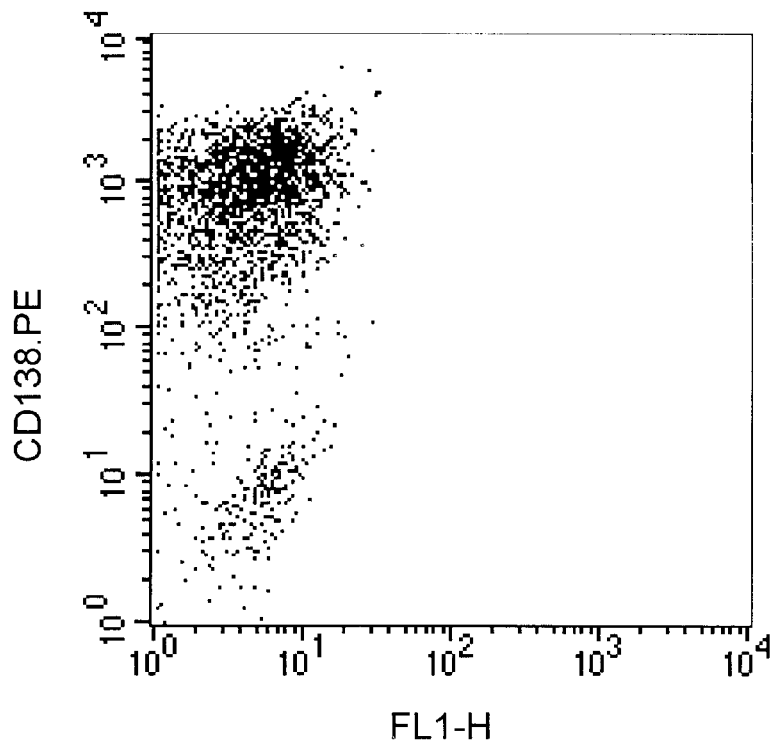
Figure 5C:
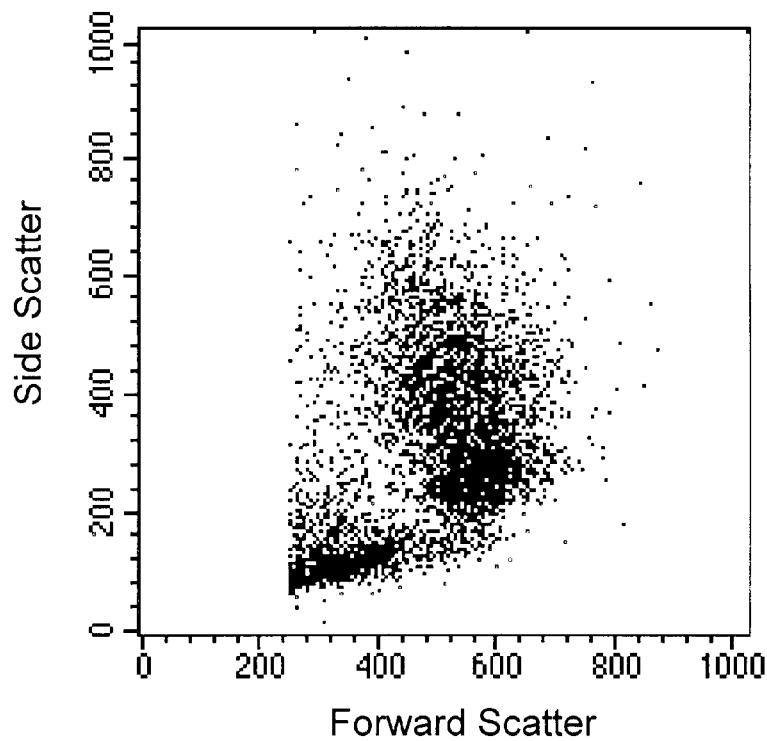
Figure 5D:
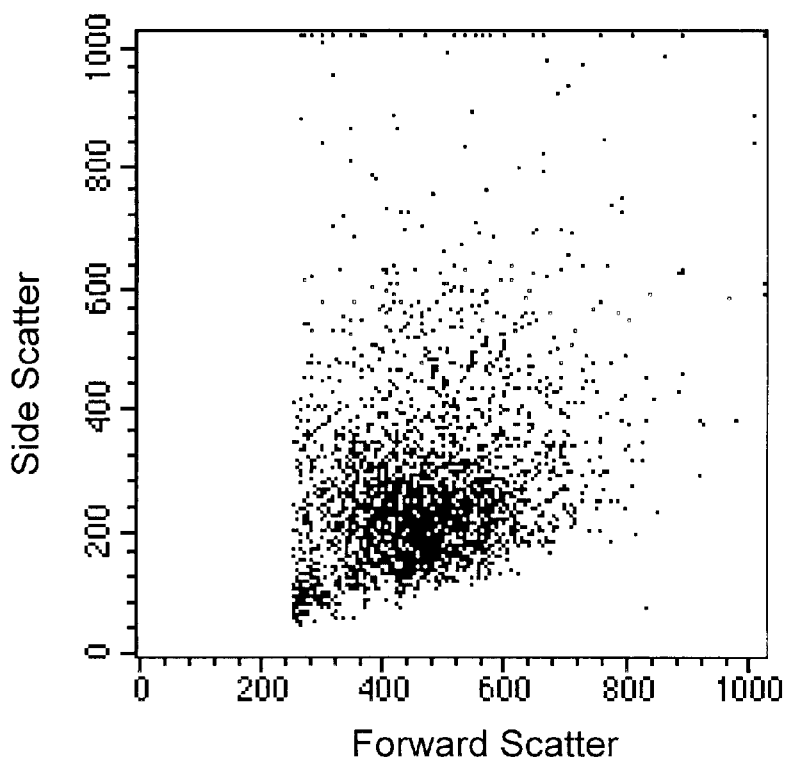
Figure 6A:
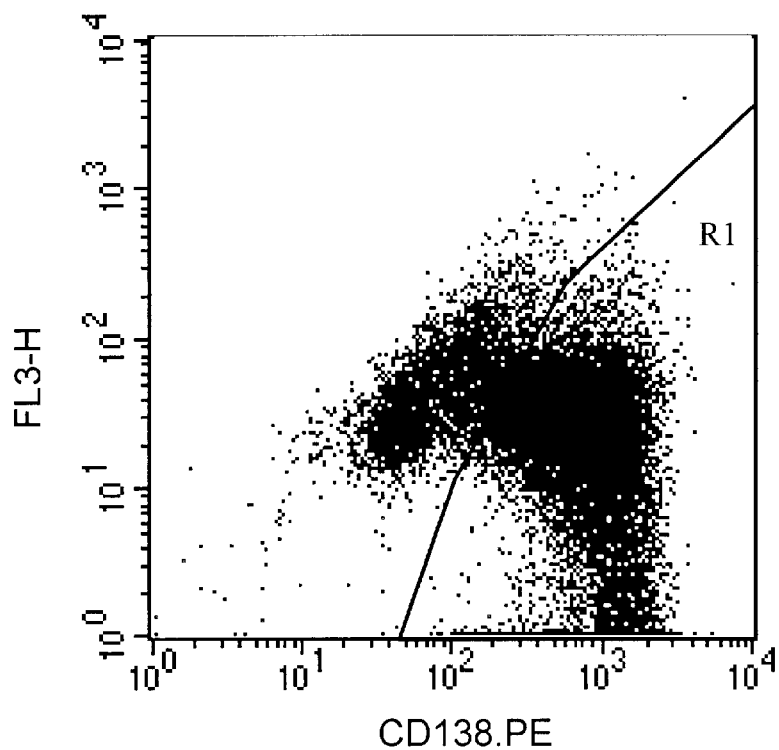
FIGS. 6A–6D are a series of FACS dot plots relating to the results of Example 2 showing intracellular staining of kappa/lambda light chains in isolated plasma cells from myeloma patients.
Figure 6B:
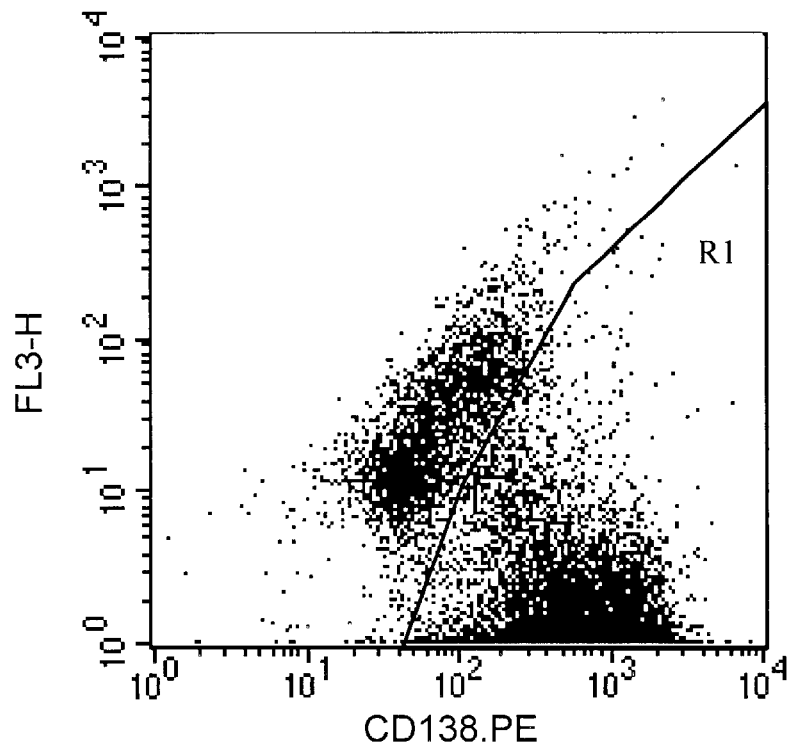
Figure 6C:
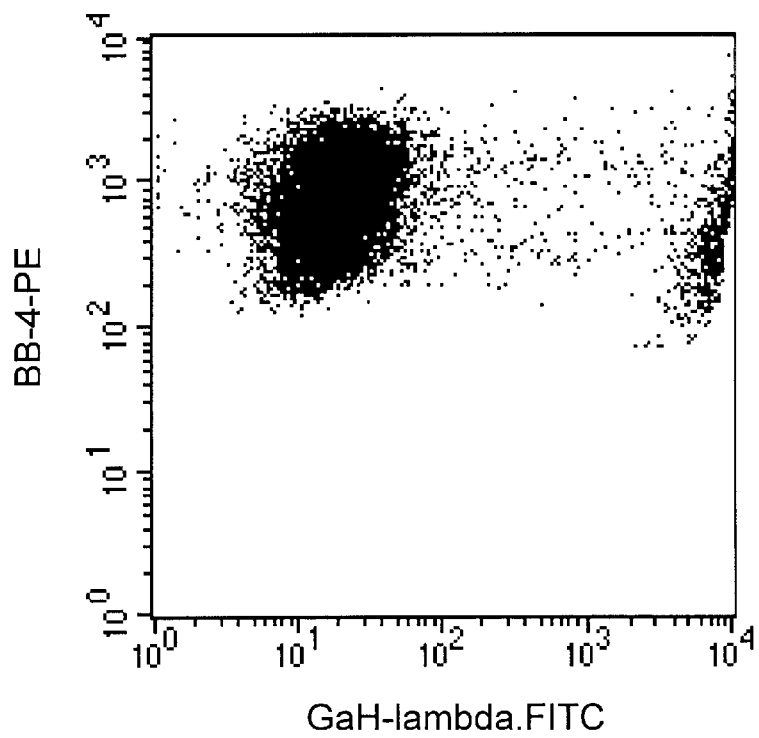
Figure 6D:
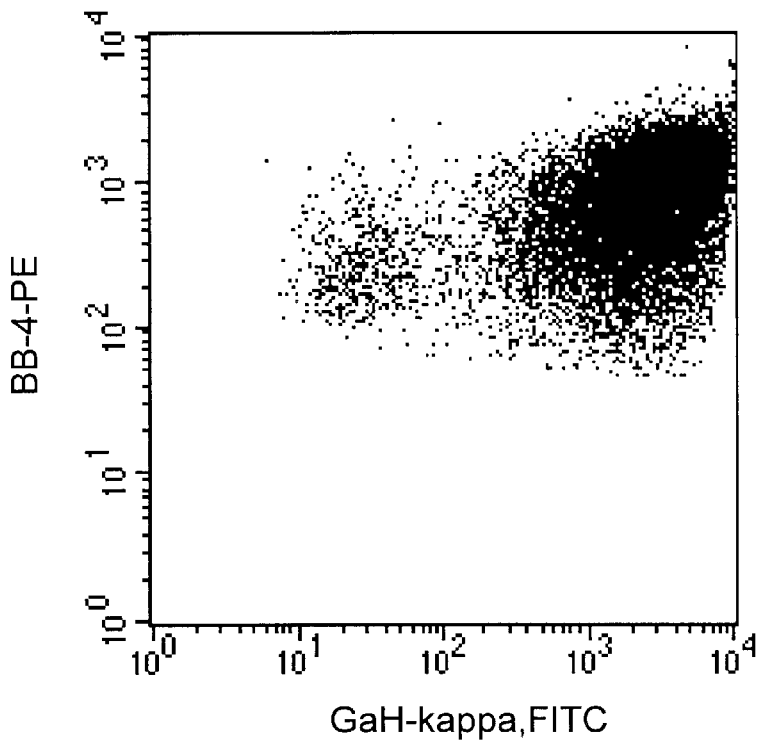

The results are shown in FIGS. 5A–5D and 6A–6D. FIGS. 5A and 5B show CD138.PE staining of live cells before and after MACS® high gradient magnetic cell separation. FIGS. 6A and 6B show CD138.PE staining versus FL3 autofluorescence of positive fraction of fixed cells after second MACS® high gradient magnetic cell separation with gating on CD138 positive cells. Dot plots 6C and 6D show intracellular staining of human immunoglobulin lambda (6C) or kappa light chain (6D) versus CD138.PE staining on gated cells. About 96% of CD138 positive cells express intracellular kappa light chain, while correspondingly 4% of CD138 positive cells express intracellular lambda light chain indicating the presence of a monoclonal tumor cell population.

Example 3

Selective Intracellular Staining of U266 Cells From a Heterogeneous Suspension

Cells of the carcinoma cell line SKBR3 were mixed with cells of the myeloma cell line U266 at a 1:1 ratio. 2×10⁶ cells were labeled with mouse anti-CD138 mAb B-B4 conjugated MicroBeads (Miltenyi Biotec GmbH, Friedrich Ebert Str. 68, D-51429 Bergisch Gladbach, Germany) and mouse anti-human epithelial antigen (HEA) MicroBeads (Miltenyi Biotec GmbH, Friedrich Ebert Str. 68, D-51429 Bergisch Gladbach, Germany) in 100 µl PBS/BSA/EDTA (Buffer) for 15 minutes at 8° C. The cells were washed and resuspended in 1 ml buffer. Then 1 ml buffer containing 4% formaldehyde (Merck) was added and incubated for 20 minutes at room temperature.

The magnetically labeled and fixed cell suspension was directly pipetted on top of a separation column in a Mini-MACS separation unit. The cell suspension was allowed to pass through the column and the column was washed with 2×500 µl buffer containing 0.5% saponin (saponin-buffer, Serva, Carl-Benz-Str. 7, 69115 Heidelberg, Germany). The effluent was collected as a negative fraction. Then 100 µl saponin-buffer containing 10 µg/ml Goat anti-human lambda.FITC (SBA, 160A Oxmoor Boulevard, Birmingham, Ala. 35209, USA) was applied to the column and incubated for 10 min at room temperature. The column was removed from the separator, and placed on a suitable container for collecting eluate. 0.5 ml buffer was pipetted on top of the column and magnetically labeled cells were flushed out using a plunger.

In parallel, 2×10⁶ cells were fixed in buffer containing 2% formaldehyde (Merck) for 20 minutes at room temperature. The cells were washed with saponin-buffer, resuspended in 15 µl saponin-buffer containing 10 µg/ml goat anti-human lambda.FITC (SBA, 160A Oxmoor Boulevard, Birmingham, Ala. 35209, USA) and incubated for 10 minutes at room temperature. The cells were washed with saponin-buffer and resuspended in buffer.

The control sample and the positive cell fractions from the MACS® high gradient magnetic cell separation were analyzed by flow cytometry. FACScan and CELLQuest research software (Becton Dickinson, Mountain View, Calif.) were used for flow cytometric analysis.

Figure 7A:
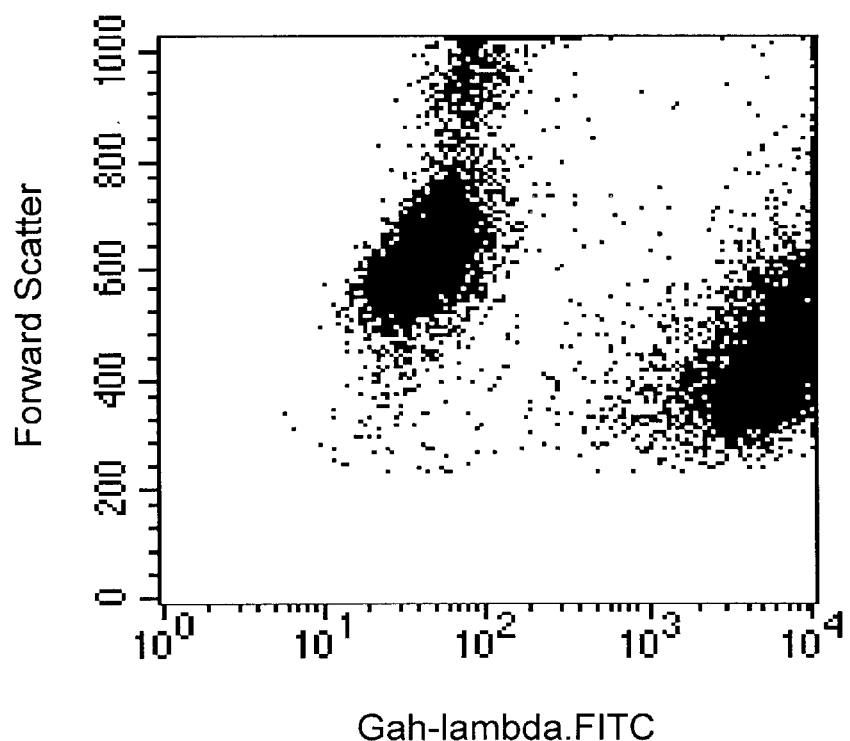
FIGS. 7A–7B are a series of dot plots relating to the results of Example 3.
Figure 7B:
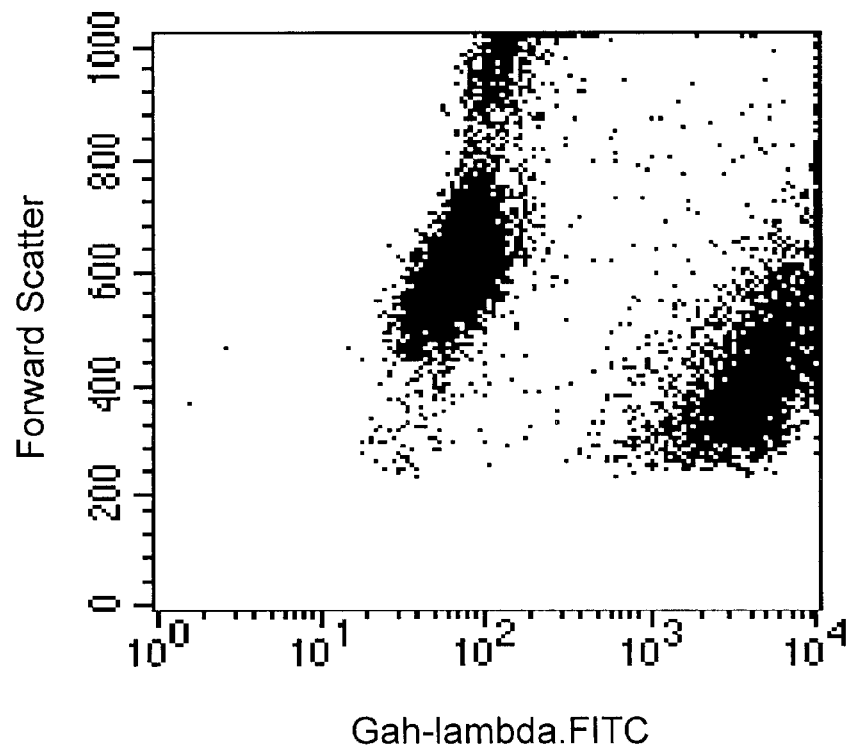
Figure 8A:
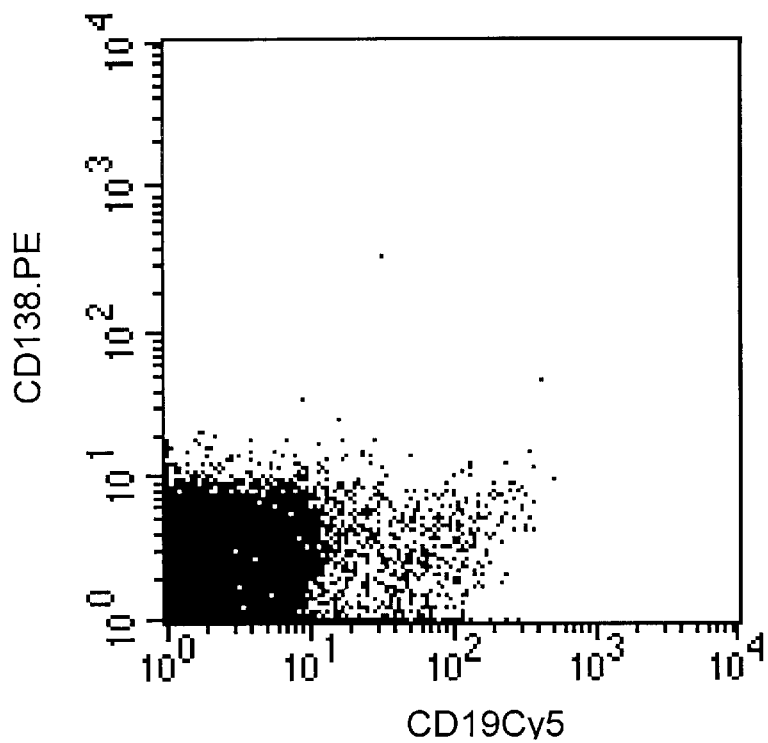
FIGS. 8A–8E are a series of FACS dot plots relating to the results of Example 4 showing staining of surface Ig upon CD138 MACS® high gradient magnetic cell separation.
Figure 8B:
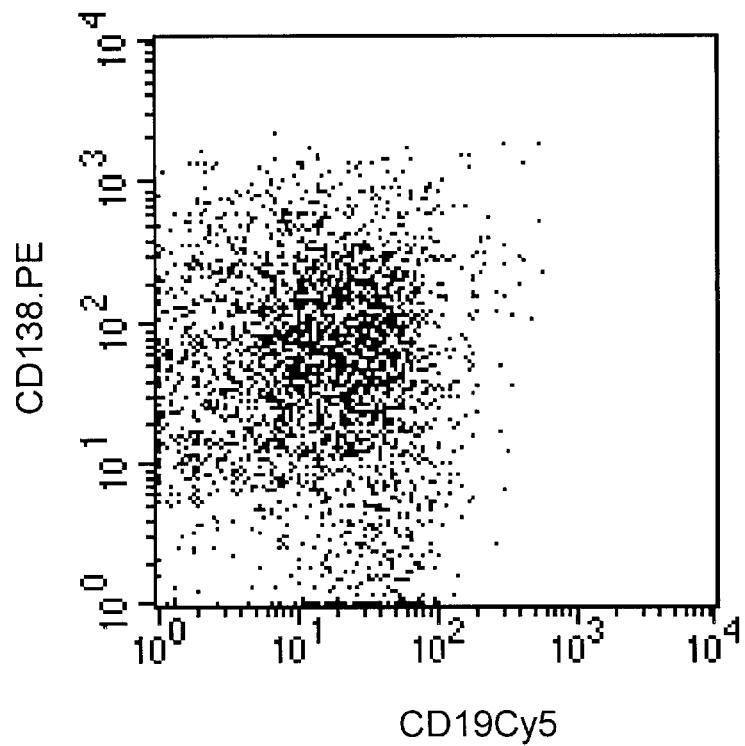
Figure 8C:
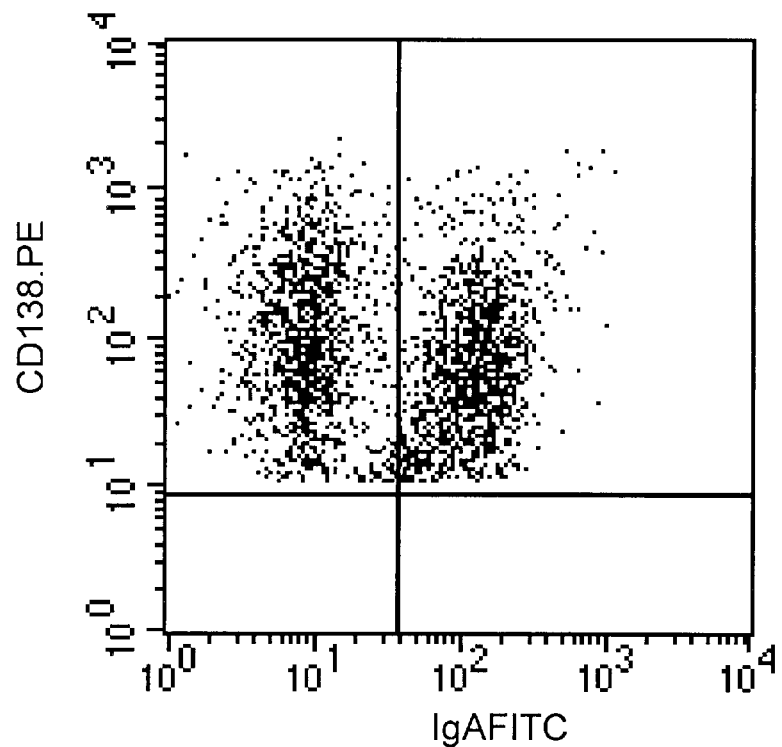
Figure 8D:
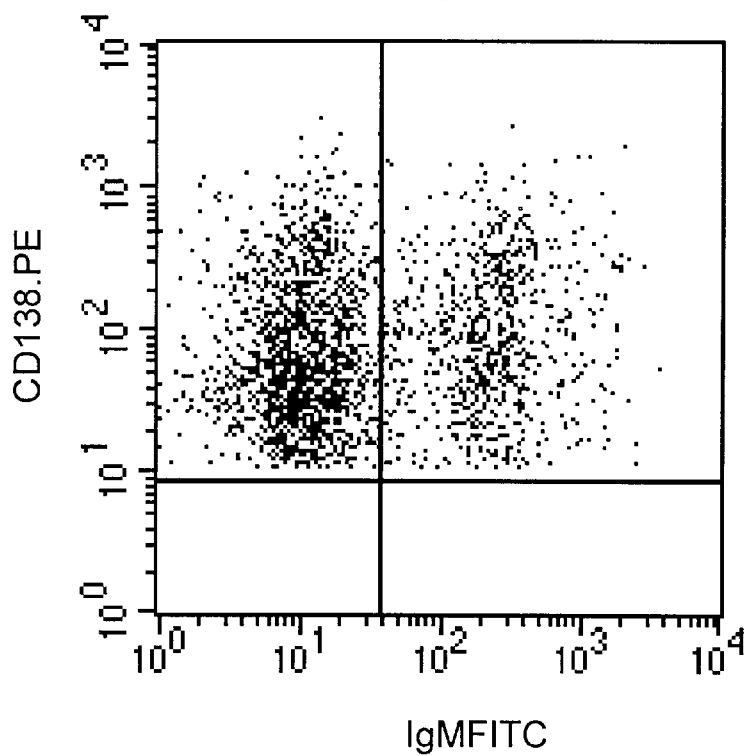
Figure 8E:
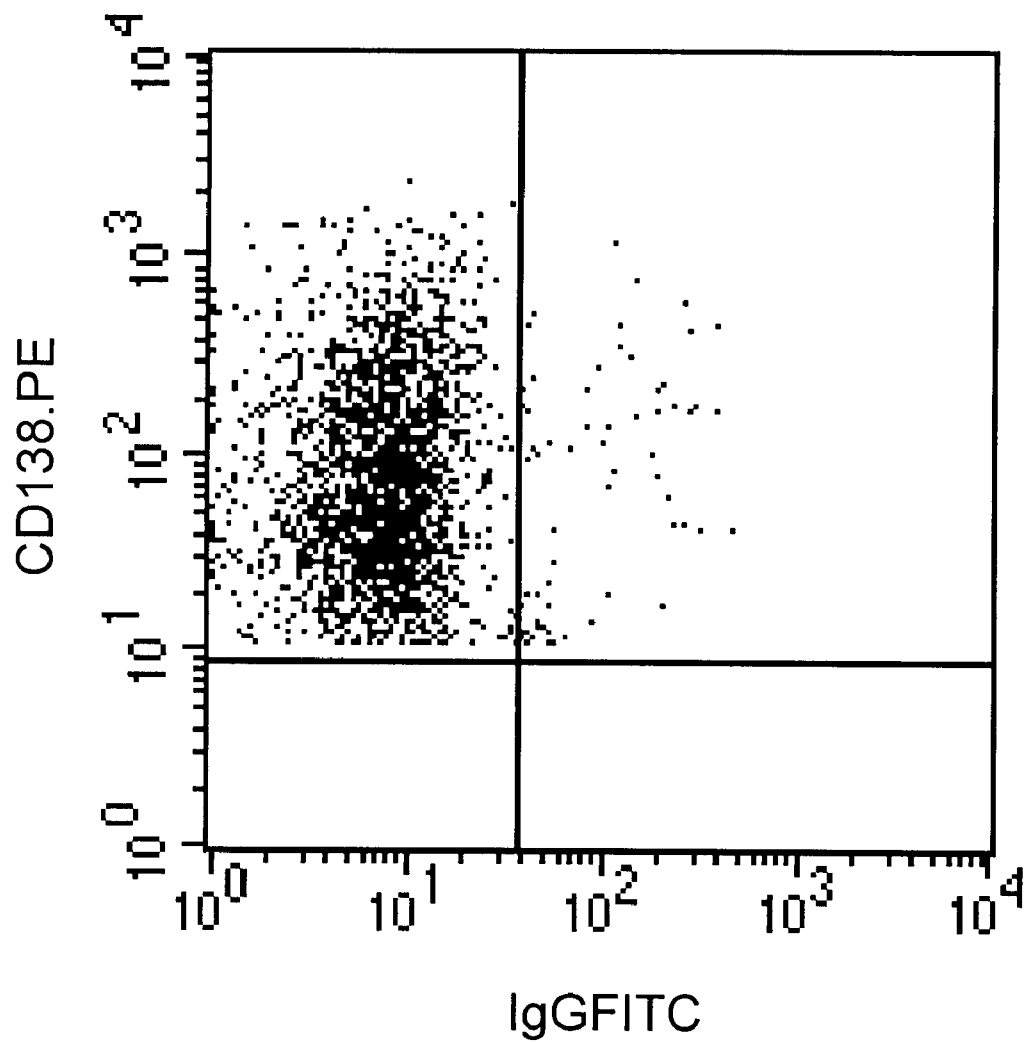

Results are shown in FIGS. 7A–7B, and in Table 2 below. FIGS. 7A and 7B show Goat anti-human lambda.FITC staining of cells stained on the column (7A) or outside the column (7B). In both samples about 50% of the cells express intracellular kappa light chain, as reported for U266 cells, with very similar staining intensities (Table 2). Thus staining of cells on the column is at least as efficient as staining in suspension.

TABLE 2

|  | mean intensity of fluorescent staining of | |
| --- | --- | --- |
|  | negative cells | positive cells |
| staining on column | 44 | 3100 |
| staining in suspension | 56 | 2647 |

Example 4

Surface Staining of Different Ig Classes on CD138 Cells, Including Streptavidin/Biotin Binding 4×10⁸ peripheral blood mononuclear cells (PBMC) were labeled with mouse anti-CD138 mAb B-B4 conjugated MicroBeads (Miltenyi Biotec GmbH, Friedrich Ebert Str. 68, D-51429 Bergisch Gladbach, Germany) in 2 ml PBS/BSA/EDTA (buffer) for 30 min at 8° C. The cells were washed and resuspended in 2 ml buffer.

CD138 positive cells were enriched with the MACS® magnetic cell separation system (Miltenyi Biotec GmbH, Friedrich Ebert Str. 68, D-51429 Bergisch Gladbach, Germany). Magnetically labeled cell suspension was pipetted on top of a separation column in a MiniMACS separation unit, cell suspension was allowed to pass through and the column was washed with 3×500 µl buffer. The effluent was collected as a negative fraction. The column was removed from the separator, and placed on a suitable container for collecting eluate. 1.5 ml buffer was pipetted on top of the column and magnetically labeled cells were flushed out using a plunger. The eluted cells were split and directly applied on top of three different separation columns (a, b and c) in MiniMACS separation units. The cell suspensions were allowed to pass through the columns and each column was washed with 2×500 µl buffer. The effluents were collected as negative fractions. Then 100 µl buffer containing Phycoerythrin conjugated mouse anti-CD138 mAb B-B4 (CD138.PE) (Miltenyi Biotec GmbH, Friedrich Ebert Str.

68, D-51429 Bergisch Gladbach, Germany), mouse anti-CD19.Cy5 and (a) 5 μg/ml mouse anti human IgA.biotin, (b) 5 μg/ml mouse anti human IgM.FITC or (c) 2 μg/ml mouse anti human IgG.FITC (all obtained from Southern Biotechnology Associates, SBA 160A Oxmoor Boulevard, Birmingham, Ala. 35209, USA) were applied to the different columns, respectively and incubated for 10 minutes at room temperature. Each column was washed with 500 μl buffer. For (a), additional 100 μl buffer containing 2 μg/ml Streptavidin.FITC were applied, followed by incubation for 10 minutes at room temperature and a washing step with 500 μl buffer. The columns were removed from separator, and placed on a suitable container for collecting eluate. 0.5 ml buffer was pipetted on top of each column and the magnetically labeled cells were flushed out from each using a plunger.

Original cells (i.e. before MACS® high gradient magnetic cell separation) and positive cell fractions of the MACS® high gradient magnetic cell separation were analyzed by flow cytometry. FACScan and CELLQuest research software (Becton Dickinson, Mountain View, Calif.) were used for flow cytometric analysis. Dead cells and cell debris were excluded according to scatter properties and staining with propidium iodide (PI; 0.3 μg/ml).

The majority, about 50%, of CD138+ cells from normal PBMC express surface IgA, while about 32% express surface IgM and about 3% express surface IgG.

Example 5

Surface Staining of CD 19 Versus CD 4 Lymphocytes Upon CD 45 Isolation Directly from Whole Blood 1 ml of heparinized human blood was labeled with 20 μl human CD45 MicroBeads (Miltenyi Biotec GmbH, Friedrich Ebert Str. 68, D-51429 Bergisch Gladbach, Germany) for 30 minutes at room temperature. Then 1 ml PBS/EDTA was added.

CD 45 positive cells were then enriched with the MACS® magnetic cell separation system (Miltenyi Biotec GmbH, Friedrich Ebert Str. 68, D-51429 Bergisch Gladbach, Germany). The magnetically labeled cell suspension was pipetted on top of a separation column in a MiniMACS separation unit. The cell suspension was allowed to pass through the column and the column was washed with 2×500 μl buffer. The effluent was collected as a negative fraction. Then 100 μl buffer containing Phycoerythrin conjugated CD19 mAb (CD19.PE) and FITC conjugated CD4 mAb (CD4.FITC) were applied to the column and incubated for 10 minutes at room temperature. The column was washed with 500 μl buffer. The column was removed from the separator, and placed on a suitable container for collecting eluate. 0.5 ml buffer was pipetted on top of each column and the magnetically labeled cells were flushed out using a plunger.

The positive cell fraction of the MACS® high gradient magnetic cell separation was analyzed by flow cytometry. FACScan and CELLQuest research software (Becton Dickinson, Mountain View, Calif.) were used for flow cytometric analysis. Dead cells, non-nucleated cells and cell debris were excluded according to scatter properties (R1 gating) and staining with propidium iodide (PI, 0.3 μg/ml) and LDS 751 (1 μg/ml) (R2 gating).

Figure 9A:
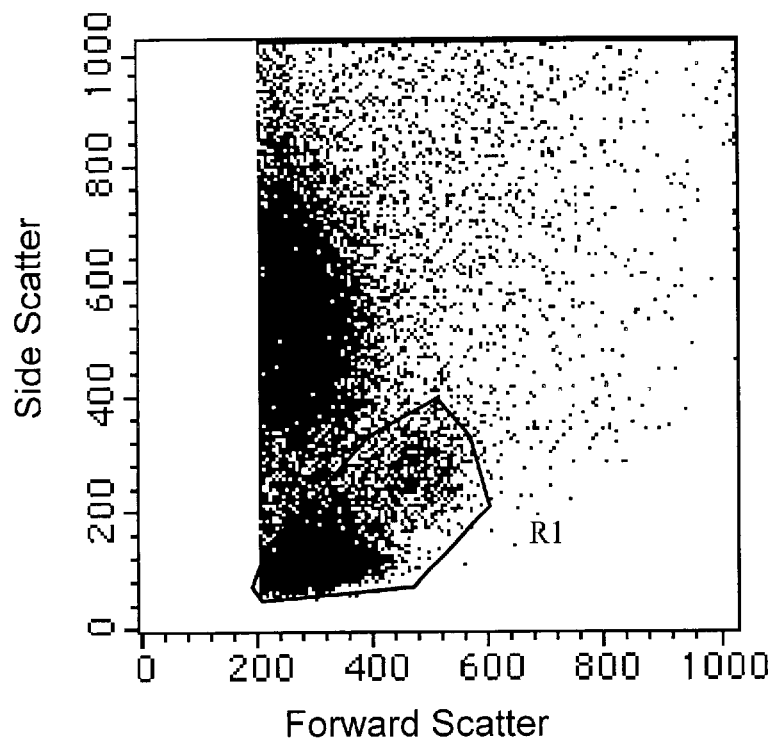
FIGS. 9A–9C are a series of FACS dot plots relating to the results of Example 5 showing immunophenotyping of lymphocytes upon CD45 MACS® high gradient magnetic cell separation from whole blood.
Figure 9B:
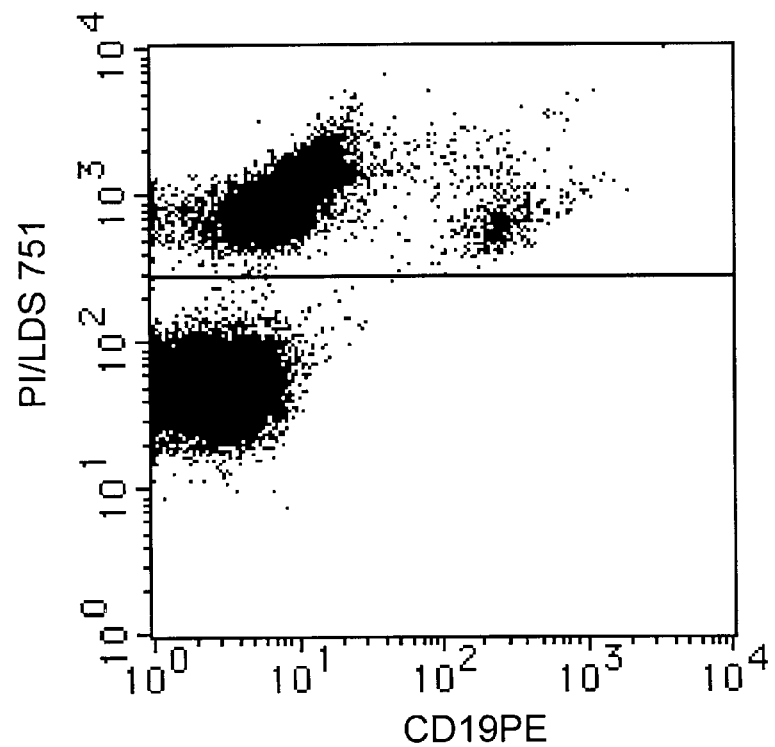
Figure 9C:
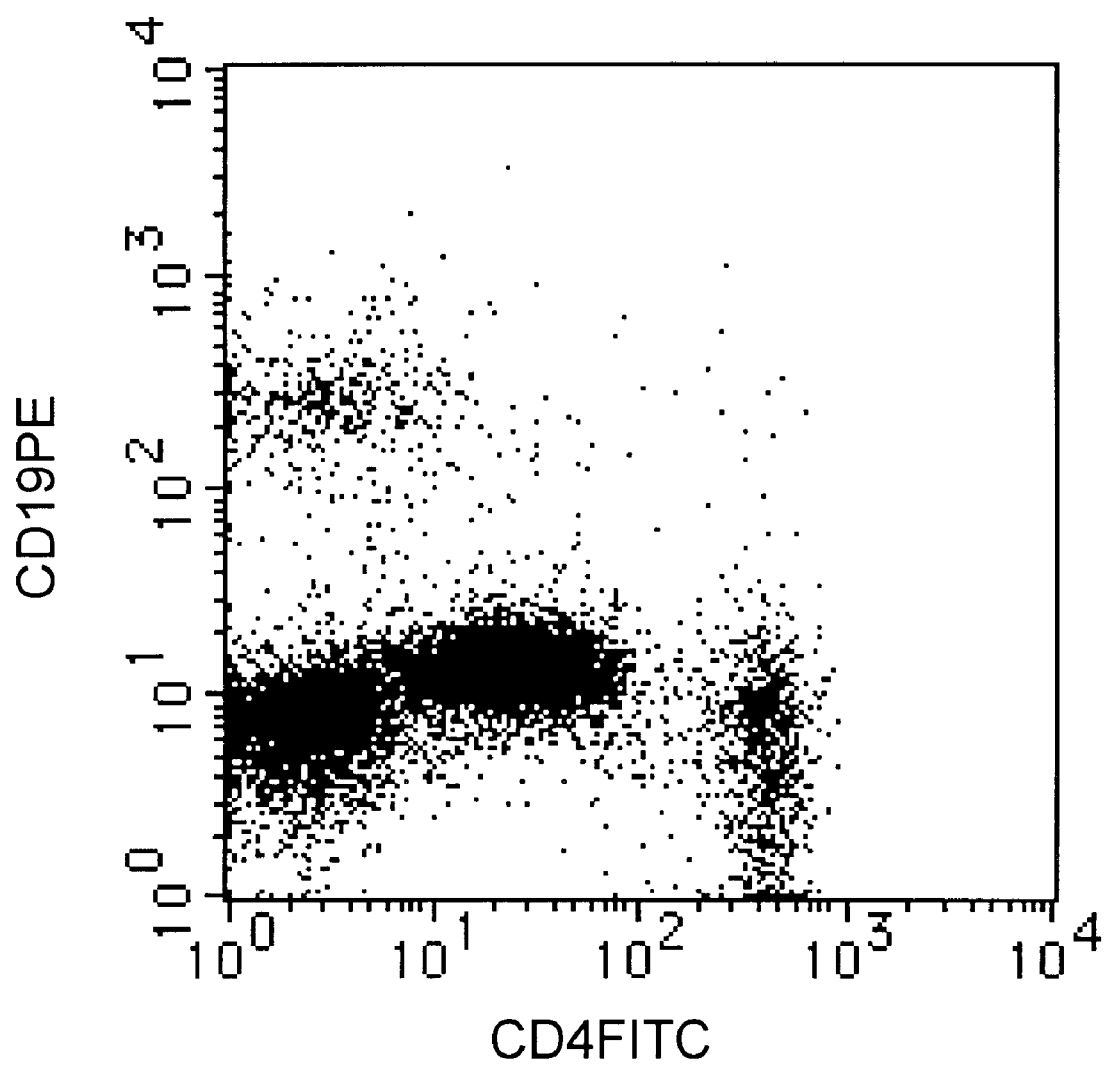

As shown in FIG. 9C, CD19+B cells, CD4++ T cells and CD4dim Monocytes can be clearly discriminated in the positive fraction. There are no significant numbers of double positive cells, which would have been expected if different subtypes of CD45+ lymphocytes like B cells, T cells or Monocytes would form stable aggregates upon CD45 MACS® high gradient magnetic cell separation and staining on the column.

Figure 10:
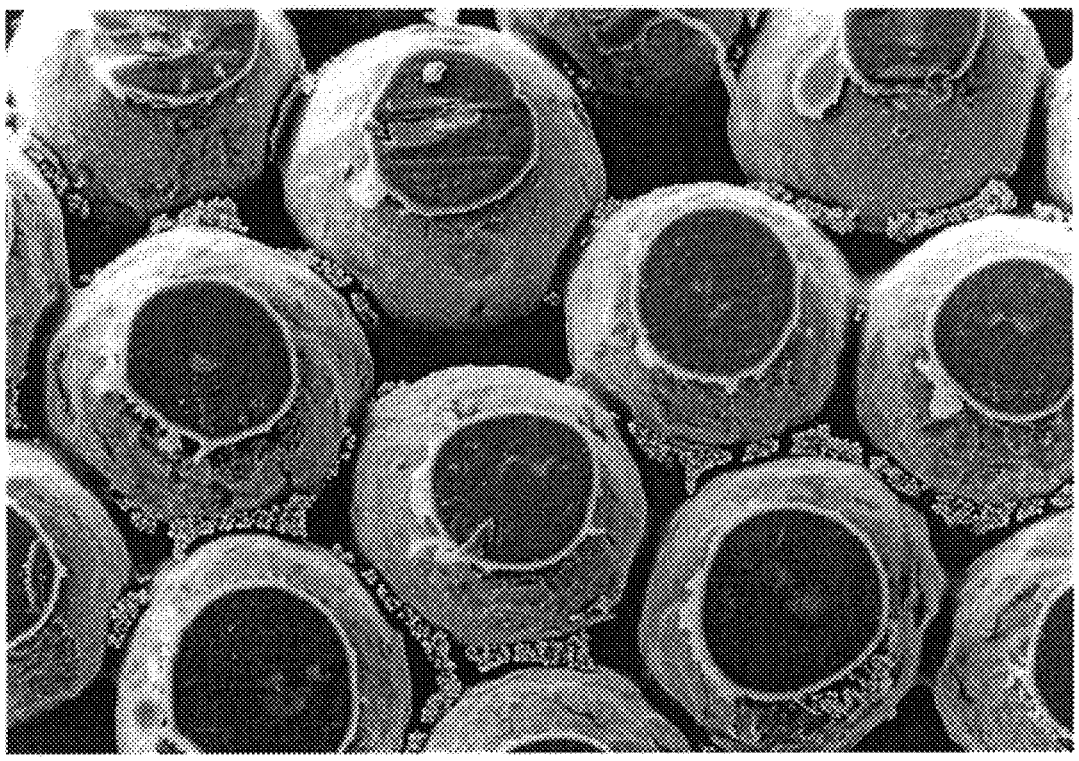
FIG. 10 is a rasterelectronmicroscopic photo of an iron sphere matrix of an MS+ column with magnetically labeled CD8+ cells attached to the matrix.

FIG. 10 is a rasterelectronmicroscopic photo of an ironsphere matrix of an MS+ column with magnetically labeled CD8+ cells attached to the matrix. FIG. 10 shows that cells are not homogeneously distributed over the whole matrix surface but concentrated in distinct areas. Cells are not immobilized as a monolayer. Instead often many cells are in very close proximity.

Although the foregoing invention has been described in detail by way of illustration and example for purposes of clarity and understanding, it will be apparent to those skilled in the art that certain changes and modifications may be practiced. Therefore, the description and examples should not be construed as limiting the scope of the invention which is delineated by the appended claims.

What is claimed is:

1. A method for modifying selected cells comprising the steps of
    (a) applying a population of cells to a high gradient magnetic separation column wherein said column comprises a matrix that is more than 50% of the total volume of the column, wherein said population of cells comprises magnetically labeled selected cells and wherein said magnetically labeled selected cells are retained by said column; and
    (b) modifying said selected cells wherein said cells are modified while retained by said column thereby producing modified, selected cells.

2. The method of claim 1 further comprising the step of removing the modified, selected cells from the column.

3. The method of claim 1, wherein the volume of the matrix is more than 60% of the total volume of the column.

4. The method of claim 1, wherein the matrix comprises ferromagnetic spheres.

5. The method of claim 2 wherein said removing is by removing said magnetic field.

6. The method of claim 1, wherein said modifying comprises intracellular staining of said selected cells.

7. The method of claim 1, wherein said modifying comprises permeabilizing said selected cells.

8. The method of claim 1, wherein said modifying comprises a second labeling of said selected cells wherein said second labeling occurs while said cells are retained on said column.

9. The method of claim 1, wherein said modifying comprises binding a biologically reactive compound to the selected cells.

10. The method of claim 9 wherein said biologically reactive compound includes antibodies, ligands, proteins, peptides, nucleic acids, polynucleotides, oligonucleotides, lectins, lipids or enzymes.

11. The method of claim 1, wherein said modifying comprises transfecting the selected cells with an expression vector.

12. The method of claim 1 wherein said modifying comprises applying an enzyme to said selected cells.

13. The method of claim 1 wherein said modifying comprises applying a pharmacological agent to said selected cells.

14. The method of claim 1 wherein said modifying comprises applying a biological modifier to said selected cells, wherein said biological modifier includes pharmacologic agents, cytokines, interleukins, hormones, growth factors, and other intercellular or intracellular signals.

15. The method of claim 1 wherein said modifying comprises applying a chemical agent to said selected cells.

16. The method of claim 1, wherein said modifying comprises applying a first and a second modifying agent to said selected cells.

17. The method of claim 2, further comprising applying the modified, selected cells to a second high gradient magnetic cell separation column such that the selected cells are retained by said second column; and modifying the selected cells wherein said cells are modified while retained by said second column.

18. The method of claim 17 further comprising the step of removing said selected cells from said second column.

19. The method of claim 4 wherein said ferromagnetic spheres are coated with a biocompatible polymer.

20. The method of claim 1 wherein said matrix comprises ferromagnetic material.

* * * * *